United States Patent [19]

Hirschfeld

[11] Patent Number: 4,568,678
[45] Date of Patent: Feb. 4, 1986

[54] SUBSTITUTED N-ALKYL IMIDAZOLES TO TREAT CONVULSIONS

[75] Inventor: Donald R. Hirschfeld, Mountain View, Calif.

[73] Assignee: Syntex (U.S.A.) Inc., Palo Alto, Calif.

[21] Appl. No.: 592,045

[22] Filed: Jun. 11, 1984

Related U.S. Application Data

[62] Division of Ser. No. 365,835, Apr. 5, 1982, abandoned.

[51] Int. Cl.⁴ ............................................. A61K 31/44
[52] U.S. Cl. .................................................. 514/297
[58] Field of Search .................. 424/273 R; 548/336; 514/297

[56] References Cited

U.S. PATENT DOCUMENTS 3,575,999  4/1971  Godefroi et al. .................. 548/336

FOREIGN PATENT DOCUMENTS 29355  5/1981  European Pat. Off. .
2706670  8/1978  Fed. Rep. of Germany .

*Primary Examiner*—Stanley J. Friedman
*Attorney, Agent, or Firm*—Annette M. Moore; Tom M. Moran

[57] ABSTRACT

This invention relates to compounds of the formula:

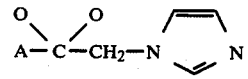

wherein A is biphenyl unsubstituted or substituted on one or both rings with one or more halo, lower alkyl, lower alkoxy or trifluoromethyl substituents; Z is ethylene unsubstituted or substituted with a single lower alkyl substituent or propylene unsubstituted or substituted with one or two lower alkyl substituents; and the pharmaceutically acceptable acid addition salts thereof. These compounds have anticonvulsant activity.

2 Claims, No Drawings

SUBSTITUTED N-ALKYL IMIDAZOLES TO TREAT CONVULSIONS

This is a division of pending U.S. application Ser. No. 365,835 filed Apr. 5, 1982, now abandoned.

BACKGROUND OF THE INVENTION

1. Field of the Invention

The present invention relates to certain N-alkyl imidazoles substituted on the alkyl chain by a cyclic ketal moiety and an optionally substituted biphenyl substituent which are useful as anticonvulsant agents in mammals. The invention also relates to pharmaceutically acceptable compositions of these compounds.

2. Related Disclosure

Some of the subject compounds are disclosed in European patent application No. 0029355 filed with the EPO Nov. 14, 1980 and published in the EPO bulletin May 27, 1981. That application discloses various 5 and 6 member ring cyclic ketals and their plant-compatible inorganic or organic acids salts and metal complexes. It also discloses methods for preparing these compounds. These compounds are stated to be antimicrobicidal agents which are particularly effective against phytopathogenic fungi. Pesticidal compositions are also disclosed therein. Additionally United Kingdom Application No. 2,030,563 recites 1-(2-(biphenyl)ethan-2-on-1-yl) imidazoles.

SUMMARY OF THE INVENTION

Useful as anticonvulsant in mammals are those compounds represented by the formula:

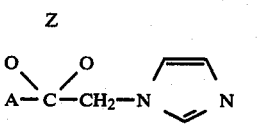
(I)

wherein A is biphenyl unsubstituted or substituted on one or both rings with one or more halo, lower alkyl, lower alkoxy or trifluoromethyl substituents; Z is ethylene unsubstituted or substituted with a single lower alkyl substituent or propylene unsubstituted or substituted with one or two lower alkyl substituents; and the pharmaceutically acceptable acid addition salts thereof.

A second aspect of the present invention is a pharmaceutical composition effective for treating convulsions in mammals which comprises a compound of formula I or a pharmaceutically acceptable acid addition salt thereof in admixture with at least one pharmaceutically acceptable excipient.

In another aspect this invention relates to a method for treating convulsions in a mammal which method comprises administering an effective amount of a compound of formula I

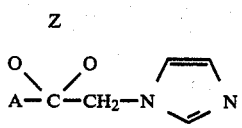
(I)

wherein
A is biphenyl unsubstituted or substituted on one or both rings with one or more halo, lower alkyl, lower alkoxy or trifluoromethyl substituents;
Z is ethylene unsubstituted or substituted with a single lower alkyl substituent or propylene unsubstituted or substituted with one or two lower alkyl substituents;
or a pharmaceutically acceptable acid addition salt thereof either alone or in admixture with a pharmaceutically acceptable excipient.

In yet a further aspect this invention relates to a process for preparing the compounds of formula I which process comprises:

(a) converting a compound of the formula

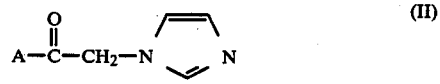
(II)

wherein A is defined above, or an acid additon salt thereof, to a dioxolane or dioxane by treatment with a 1,2-diol or 1,3-diol; or (b) converting a compound of the formula

(II)

wherein A and Z are defined above, and X is a leaving group, to an imidazole by treatment with imidazole or a derivation thereof; or (c) converting the free base of the compound of formula I with an acid to a pharmaceutically acceptable acid addition salt; or (d) converting a salt of the compound of formula I with a base to the corresponding free base; or (e) converting a salt of the compound of formula I to another salt.

DESCRIPTION AND PREFERRED EMBODIMENTS

Various terms used herein should be understood to read according to the following annotations unless otherwise specified.

The term "biphenyl" herein means that radical comprising two phenyl rings wherein one is substituted directly onto the first at some position which may be ortho, meta, or para to the position on the first ring which is bonded to the N-alkyl imidazole moiety. Preferred is that biphenyl radical wherein the second phenyl ring is substituted para to the position at which the first phenyl ring is substituted on the N-alkyl imidazole moiety.

Numbering for the biphenyl ring positions follow conventional numbering, that is whole numbers are used to reference substituent positions on the N-alkylimidazole substituted ring while primed whole numbers denote substituent position on the second ring.

"Unsubstituted or substituted on one or both rings" means that both phenyl rings may contain only hydrogen; or one ring may be substituted with one or more of one of the enumerated substituents while the other ring is unsubstituted; or both rings may be substituted with the one or more of the same substituents; or one ring may be substituted with one or more of the same substituents while the other ring is substituted with one or more different substituents all of which are the same; or one ring may have two or more different substituents while the other ring is unsubstituted or substituted with at least one same or different substituent; or both rings may be substituted with two or more different substituents. For example, the first ring may be substituted with chloro groups at positions 2 and 6 while the second ring is unsubstituted. Alternatively, both rings may substituted with one or more chloro groups. In a third instance, the first ring may be substituted with, for example, two chloro groups while the second ring may be substituted with an alkoxy group. Furthermore, one ring, for example, the second ring, may have, for example, a halo and alkyl substituent while the other ring is unsubstituted or substituted with halo or alkyl alone or both halo and alkyl.

The term "lower alkyl" refers to a straight or branched chain monovalent substituent consisting solely of carbon and hydrogen with no unsaturation and containing from 1 to 4 carbon atoms. Examples of such alkyl groups are methyl, ethyl, n-propyl, i-propyl, n-butyl, t-butyl, and the like. The term "lower alkoxy" refers to a lower alkyl chain as described above having no more than four carbons this radical being linked to another carbon atom by oxygen commonly known as an ether linkage in the chemical arts. Examples of such groups include methoxy, ethoxy, n-propoxy, i-propoxy, n-butoxy, t-butoxy and the like. The term "halo" means fluoro, chloro, bromo and iodo.

"Pharmaceutically acceptable acid addition salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

Compounds of formula I wherein Z is substituted ethylene or propylene may exist as may geometric isomers (i.e., cis and trans) relative to the ketal ring. Both isomers and mixtures thereof, where present, are to be included in the scope of this invention. Any discussion of synthetic routes should be understood to include, where appropriate, both geometric isomers unless specifically stated otherwise. If desired the respective geometric isomers of formula I may be separated by methods well known in the art. Such methods may be, for example, chromatography, fractional crystallization, high-pressure liquid chromatography, and the like.

Furthermore, a chiral center is present at the 4-position of the ketal ring when a substituent is present there. Therefore, synthesis may produce an optical isomer or a racemic mixture. The scope of this invention covers both forms, but unless otherwise noted the racemic mixture will be present.

If desired, the compounds herein may be resolved into their optical antipodes by conventional resolution means; for example by separation (e.g. fractional crystallization) of the diastereomeric salts formed by the reaction of these compounds with optically active acids. Exemplary of such optically active acids are the optically active forms of camphor-10-sulfonic acid, 2-bromocamphor-$\pi$sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means to afford the respective optical isomers of the compounds of formula I. Alternatively, use of a resolved diol permits preparation of compounds of formula I in optically active form. Resolution of such diols is readily accomplished by standard methods well known in the art.

The compounds of formula I herein and the pharmaceutically acceptable acid addition salts affect the central nervous system (CNS) in mammals. Specifically they have use as anticonvulsant agents. Initial anticonvulsant activity is determined using the maximal electroshock seizure test (J. Pharmacol. Exp. Ther. 106: 319–330, 1952) or modifications thereof.

Administration of the active compounds and salts described herein can be via any of the accepted modes of administration for agents which are CNS active. These methods include oral, parenteral and otherwise systemic or aerosol forms.

Depending on the intended mode of administration, the compositions used may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of formula I or a pharmaceutically acceptable acid addition salt thereof and, in addition, may include other medicinal agents, pharmaceutical agents, carriers, adjuvants, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s) in an amount effective to alleviate the symptoms of the subject being treated or prevent their onset.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like. Such compositions may contain 1–99% active ingredient, preferably 20–80%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

In general, for systemic (e.g., oral or parenteral) administration, it is expedient to administer the active ingredient in amounts between 0.1 and 300 mg/kg body weight per day, preferably between about 0.3 and 100 mg/kg body weight per day, preferably distributed over several applications (e.g., in three individual doses in order to achieve the most effective results).

The compounds of formula I may be considered to consist of two subclasses, those of formula Ia and Ib shown below

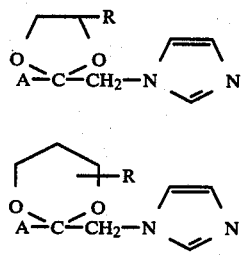

wherein R is hydrogen or a lower alkyl group and A is defined above.

One group of preferred compounds of formula I is that group wherein A is an unsubstituted biphenyl and Z is ethylene or propylene or lower alkyl substituted ethylene or propylene; and the pharmaceutically acceptable acid addition salts thereof.

Another group of preferred compounds of formula I is that group wherein A is 4-biphenyl substituted with 1-3 halo or lower alkyl groups. When two or more substituents are present it is preferred that they are the same and are halo or methyl. Most preferred within this group are those compounds wherein the 4-biphenyl is substituted with a single substituent, preferably halo or lower alkyl, most preferably at the 4' position.

Within the above two preferred groups, more preferred compounds of formula I are those wherein Z is ethylene or propylene or ethylene or propylene substituted with a single straight chain alkyl group at the 4-position or propylene substituted with two methyl groups at the 5-position. Compounds wherein Z is unsubstituted ethylene or propylene are particularly preferred.

Most preferred compounds of formula I are
1-[(2-(4-biphenyl)-1,3-dioxolan-2-yl)methyl]imidazole;
1-[(2-(4'-chloro-4-biphenyl)-1,3-dioxolan-2-yl)methyl]imidazole;
1-[(2-(4'-methyl-4-biphenyl)-1,3-dioxolan-2-yl)methyl]imidazole;
1-[(2-(4-biphenyl)-4-methyl-1,3-dioxolan-2-yl)methyl]imidazole;
1-[(2-(4-biphenyl)-4-n-butyl-1,3-dioxolan-2-yl)methyl]imidazole;
1-[(2-(4-biphenyl)-1,3-dioxan-2-yl)methyl]imidazole;
1-[(2-(4-biphenyl)-4-methyl-1,3-dioxan-2-yl)methyl]imidazole;
1-[(2-(4-biphenyl)-5-methyl-1,3-dioxan-2-yl)methyl]imidazole;
1-[(2-(4-biphenyl)-5,5-dimethyl-1,3-dioxan-2-yl)methyl]imidazole;
1-[(2-(2-biphenyl)-1,3-dioxolan-2-yl)methyl]imidazole; and
1-[(2-(3-biphenyl)-1,3-dioxolan-2-yl)methyl]imidazole.

PREPARATIONS AND EXAMPLES

Compounds of formula I may be prepared by various synthetic routes but as disclosed herein, a preferred method is to form the 2-(biphenyl)substituted N-alkylimidazole of formula II then making the cyclic ketal therefrom.

The compounds of formula II may be prepared from a suitable ketone represented by formula III as depicted in Reaction Scheme A wherein A and Z are defined above and X is a leaving group, such as halo (chloro, bromo, iodo) or a reactive ester, e.g., a sulfonate ester.

REACTION SCHEME A

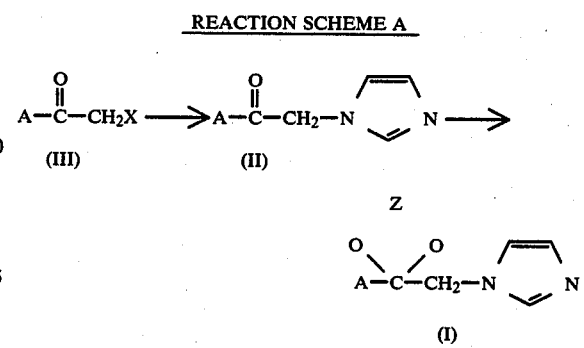

(a) The halo ketones of formula III wherein A is unsubstituted biphenyl are known or are readily prepared using the methods disclosed (for the 4-biphenyl isomer) in European Patent Application No. 0,029,355.

The compounds of formula III, insofar as they may not be known or readily available, may be prepared by a number of standard methods known in the art, e.g. from the corresponding methyl ketone or carboxylic acid derivatives. For example, treatment of a methyl ketone with a halogenating agent, preferably a brominating agent is productive of compounds of formula III wherein X is chloro or bromo. Methods for effecting their transformation are described in U.S. Pat. No. 4,078,071 which is incorporated herein by reference. Alternatively, conversion of an acid of formula A—COOH (wherein A is as defined above) may be accomplished by treatment of the corresponding acid halide with diazomethane, followed by treatment of the resulting diazoketone with HX (X equals halo) to give the compound of formula III wherein X is halo. Many appropriately substituted biphenyls containing acetyl or methoxycarbonyl substituents may be obtained by methods well known in the art, particularly, e.g. the Ullmann reaction [see e.g., Synthesis, pp 9–21 (1974); Chemical Reviews, 64, pp.613–632 (1964); Quarterly Reviews of the Chemical Society, 19, pp 101–107, (1965)] and the Gomberg-Bachman Reaction [see Chemical Reviews, 57, pp 77–122 (1957); Organic Reactions, Vol 2, pp 224–261 (1944)]. These reactions may produce a ketone of the formula $ACOCH_3$, but are particularly useful in preparing compounds having a —COOMe substituent, convertible by hydrolysis to the acid and thus to the compounds of formula III as described above.

Yet another useful method for producing certain compounds of formula III consists of treatment of a compound of formula AH (A being as described above) with an acid halide under Friedel-Crafts conditions, e.g. as described in "Friedel-Crafts and Related Reactions" (Ed. Olah) Vol III, part I, pp 238–240 (1964). Use of acetyl chloride permits preparation of the compounds A—$COCH_3$, while the similiar reaction using chloroacetyl chloride or bromide for example, is productive of the compounds of formula III wherein X is chloro or bromo directly.

It will be obvious to those skilled in the art that a number of routine transformations are possible following preparation of substituted biphenyls which further increase the scope of the standard reaction, e.g. reduction of nitro groups followed by diazotization and displacement by halo or hydrogen, reductive removal of halogen, etc.

The imidazole ketones of formula II are prepared according to the methods disclosed in European patent application No. 0,029,355 and U.S. Pat. No. 4,078,071 which are incorporated herein by reference.

The compounds of formula II are converted to the compounds of formula I by forming the cyclic ketal as the last reaction step. This reaction may be carried out by a number of methods well known in the art, for example, treatment of the ketone with at least one mole, but preferably an excess of a diol in the presence of 1.02 molar equivalents to 2 molar equivalents of an acid or a Lewis acid, for example, hydrogen chloride, zinc chloride, boron trifluoride or p-toluenesulfonic acid, with or without removal of water. When the acid addition salt of compounds of formula II is used, correspondingly less acid or Lewis acid (i.e. 0.02 to 1 molar equivalents) is required. In the preferred embodiment of the ketalization, the two reaction components are refluxed for several hours together with an azeotrope-former in one of the customary organic solvents. Suitable azeotrope-formers are, for example, benzene, toluene, xylene, chloroform, or carbon tetrachloride.

A particularly useful method for ketalizing compounds of formula II is that described in Synthesis, pp. 23-26, 1974. A ketone of formula III is reacted with the described dihydric alcohol in a mixture containing an excess of a simple alcohol, for example methanol, ethanol, 1-butanol or benzyl alcohol in the presence of a corresponding amount of acid or Lewis acid as described above to form the cyclic ketal.

Compounds of formula I may also be prepared by the procedure depicted in the following reaction scheme.

REACTION SCHEME B

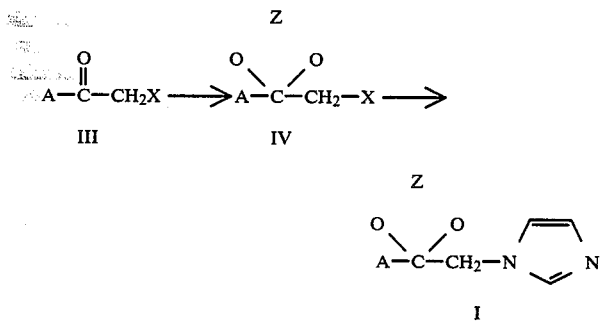

wherein A, Z and X are as previously defined.

The halo ketones of formula III are ketalized to compounds of formula IV under similar reaction conditions to those described above for the ketalization of compounds of formula II except that only a catalytic amount of acid or Lewis acid, e.g. about 0.01 to about 0.2 molar equivalents is used. Alernatively, the haloketals of formula IV may be prepared by ketalization of a ketone of formula ACOCH$_3$, followed by halogenation of the resulting ketal.

The haloketals of formula IV are then converted to the subject compounds of formula I by reaction which imidazole or a metal salt thereof, e.g., an alkali metal salt such as the sodium salt thereof. The reaction using imidazole is carried out using 1-5 equivalents of imidazole preferably in an inert polar organic solvent such as dimethylformamide, dimethylacetamide, dimethyl sulfoxide, acetonitrile and the like at a temperature of about 25° to 180° C., preferably from about 60° to 160° C. optionally in the presence of an alkali metal iodide. When a metal salt of imidazole is used, this is preferably an alkali metal salt, e.g., the sodium salt. The reaction is carried out using an equivalent amount of the salt, or an excess, in a polar inert organic solvent (e.g., dimethylformamide, dimethyl sulfoxide, etc.) at a temperature between about 0° and 150° C., preferably from about 25° C. to about 120° C.

The dihydric alcohols used in the above reaction sequences are generally available, e.g. from Aldrich Chemical Co. The 1,2-diols which are not readily available may be prepared according to known procedures as described in British Patent No. 1,528,639. The 1,3-diols which are not readily available may be prepared according to the Prins reaction as described in the Merck Index, 9th Ed., 1976, ONR-71, or as described in European Patent Application No. 0,029,355.

The subject compounds of the instant invention can be isolated as free bases; however, since many of the compounds in base form are oils, it is often more convenient to isolate and further characterize the compounds as acid addition salts.

The compounds of formula I in free base form may be converted to the acid addition salts by treating the free base with a stoichiometric amount or excess of the appropriate organic or inorganic acid exemplified above, such as, for instance hydrochloric acid, nitric acid, oxalic acid and the like. Typically, the free base is dissolved in an organic solvent such as ether, ethyl acetate, acetone or methanol, and the acid added thereto. The temperature is maintained between about 0° C. and 100° C., preferably room temperature. The resulting acid addition salt precipitates spontaneously or may be brought out of solution with a less polar solvent.

The acid addition salts of the compounds of formula I may be converted to the corresponding free base by treating with a stoichiometric amount or an excess of a suitable base, such as potassium carbonate or sodium hydroxide, typically in the presence of aqueous solvent, and at a temperature of between about 0° C. and 100° C. The free base form is isolated by conventional means, such as extraction with an organic solvent.

Salts of the compounds of formula I may be interchanged by taking advantage of differential solubilities of the salts, volatilities or acidities of the acids, or by treating with the appropriately loaded ion exchange resin. For example, the interchange is effected by the reaction of a salt of the compounds of formula I with a slight stoichiometric excess of an acid of a lower pKa than the acid component of the starting salt. This conversion is carried out at a temperature between about 0° C. and the boiling point of the solvent being used as the medium for the procedure.

The following specific preparations and examples are illustrative of present invention and should not be considered as limitative thereof in any manner.

PREPARATION 1

This preparation exemplifies the reaction set out in Reaction Scheme A for converting formula III compounds to compounds of formula II.

To a slurry of imidazole (24.7 g) in 30 ml dry dimethylformamide at 0° C. was added 4-bromoacetylbiphenyl (20.0 g) portionwise with stirring. The mixture was allowed to come to room temperature overnight and poured into 1 l. of water. The resulting white solid was filtered off, washed with water, dried in air and chromatographed on silica gel eluting with 6% methanol/methylene chloride to give 13.0 g of pure 1-[2-(4-biphenyl)ethan-2-on-1-yl)imidazole. The hydrochloride salt was precipitated from acetone using ethereal hydrogen chloride and recrystallized from ethyl acetate/methanol, m.p. 210°–240° C.

Similarly, proceeding as above, but substituting the appropriate haloacetyl substituted or unsubstituted biphenyl in place of the 4-bromoacetylbiphenyl there may be prepared the following compounds:

1-[2-(2-biphenyl)ethan-2-on-1-yl]imidazole;
1-[2-(3-biphenyl)ethan-2-on-1-yl]imidazole;
1-[2-(4'-methoxy-4-biphenyl)ethan-2-on-1-yl]imidazole;
1-[2-(4'-chloro-4-biphenyl)ethan-2-on-1-yl]imidazole;
1-[2-(2'-methyl-4'-methoxy-4-biphenyl)ethan-2-on1-yl]imidazole;
1-[2-(2',4'-dimethoxy-4-biphenyl)ethan-2-on-1-yl]imidazole;
1-[2-(3'-chloro-4'-methoxy-4-biphenyl)ethan-2-on-1-yl]imidazole;
1-[2-(4'-propyl-4-biphenyl)ethan-2-on-1-yl]imidazole;
1-[2-(4'-trifluoromethyl-4-biphenyl)ethan-2-on-1-yl]imidazole;
1-[2-(4'-chloro-2-biphenyl)ethan-2-on-1-yl]imidazole;
1-[2-(4-fluoro-2-biphenyl)ethan-2-on-1-yl]imidazole;
1-[2-(2,5-diethyl-4'-methoxy-4-biphenyl)ethan-2-on-1-yl]imidazole; and
1-[2-(3',4'-dimethyl-2-biphenyl)ethan-2-on-1-yl]imidazole.

PREPARATION 2

With reference to Reaction Scheme B, compounds of formula IV may be prepared by the following method.

A mixture of 4-bromoacetylbiphenyl (5.5 g), ethylene glycol (1.36 g), n-butanol (8.0 g) and p-toluenesulfonic acid (400 mg) in toluene (45 ml) were heated under reflux overnight with stirring using a Dean-Stark separator. When the separation of water was complete, the side arm of the separator was dried, filled with 3A molecular sieves, and heating continued overnight. The resulting mixture was made basic with aqueous sodium carbonate, the organic phase separated and the aqueous layer extracted with ether (2×75 ml). The combined organic layers were washed, dried (magnesium sulfate) and evaporated to give 2-(4-biphenyl)-2-bromomethyl-1,3-dioxolane.

Similiarly proceeding as above, but substituting the appropriate diol and the appropriate α-halo ketone in place of 4-bromoacetylbiphenyl there may be prepared, for example, the following compounds:

2-(4-biphenyl)-2-bromomethyl-1,3-dioxolane;
2-(4-biphenyl)-2-bromomethyl-4-methyl-1,3-dioxolane;
2-(4-biphenyl)-2-bromomethyl-4-ethyl-1,3-dioxolane;
2-(4-biphenyl)-2-bromomethyl-4-n-propyl-1,3-dioxolane;
2-(4-biphenyl)-2-bromomethyl-4-n-butyl-1,3-dioxolane;
2-(4'-methyl-4-biphenyl)-2-bromomethyl-1,3-dioxolane;
2-(4'-biphenyl)-2-bromomethyl-4-methyl-1,3-dioxolane;
2-(4'-chloro-4-biphenyl)-2-bromomethyl-1,3-dioxolane;
2-(4'-methoxy-4-biphenyl)-2-bromomethyl-4-ethyl-1,3-dioxolane;
2-(2-biphenyl)-2-bromomethyl-1,3-dioxolane;
2-(3-biphenyl)-2-bromomethyl-1,3-dioxolane;
2-(2-chloro-4-biphenyl)-2-bromomethyl-4-n-butyl-1,3-dioxolane;
2-(4-biphenyl)-2-bromomethyl-1,3-dioxane;
2-(4-biphenyl)-2-bromomethyl-5,5-dimethyl-1,3-dioxane;
2-(4-biphenyl)-2-bromomethyl-4-methyl-1,3-dioxane;
2-(4'-methyl-4-biphenyl)-2-bromomethyl-1,3-dioxane;
2-(4-biphenyl)-2-bromomethyl-4-ethyl-1,3-dioxane;
2-(4'-chloro-4-biphenyl)-2-bromomethyl-1,3-dioxane; and
2-(4-biphenyl)-2-bromomethyl-4-n-butyl-1,3-dioxane.

EXAMPLE I

This example illustrates the conversion of compounds according to Preparation 2 into the N-alkylimidazoles of formula I.

2-(4-biphenyl)-2-bromomethyl-1,3-dioxolane (3.06 g) and imidazole (2.8 g) in dimethyl formamide were heated in dry dimethylacetamide at reflux with stirring under nitrogen for 4 days. The solvent was removed in vacuo and the residue treated with water and the product extracted with ethyl acetate (3×75 ml). The combined extracts were washed, dried (MgSO$_4$), evaporated and the residue chromatographed on silica gel eluting with 5% methanol in methylene chloride to give 1-[(2-(4-biphenyl)-1,3-dioxolan-2-yl)methyl]imidazole.

Similarly, proceeding as above, but substituting the appropriate dioxolane or dioxane in place of 2-(4-biphenyl)-2-bromomethyl-1,3-dioxolan there may be prepared, for example, the following compounds:

1-[(2-(4'-butyl-4-biphenyl)-1,3-dioxolan-2-yl)methyl]imidazole;
1-[(2-(4'-methoxy-4-biphenyl)-1,3-dioxolan-2-yl)methyl]imidazole;
1-[(2-(4-biphenyl)-4-methyl-1,3-dioxolan-2-yl)methyl]imidazole;
1-[(2-(4'-fluoro-4-biphenyl)-4-methyl-1,3-dioxolan-2-yl)methyl]imidazole;
1-[(2-(4'-trifluoromethyl-4-biphenyl)-4-methyl-1,3-dioxolan-2-yl)methyl]imidazole;
1-[(2-(4-biphenyl)-4-n-butyl-1,3-dioxolan-2-yl)methyl]imidazole;
1-[(2-(4'-fluoro-4-biphenyl)-1,3-dioxan-2-yl)methyl]imidazole;
1-[(2-(4'-chloro-4-biphenyl)-1,3-dioxan-2-yl)methyl]imidazole;
1-[(2-(4-biphenyl)-4-methyl-1,3-dioxan-2-yl)methyl]imidazole;
1-[(2-(4'-fluoro-4-biphenyl)-4-methyl-1,3-dioxan-2-yl)methyl]imidazole;
1-[(2-(4'-t-butyl-4-biphenyl)-5,5-dimethyl-1,3-dioxan-2-yl)methyl]imidazole;
1-[(2-(4'-trifluoromethyl-4-biphenyl)-5,5-dimethyl-1,3-dioxan-2-yl)methyl]imidazole;
1-[(2-(3'-chloro-4'-methoxy-4-biphenyl)-1,3-dioxolan-2-yl)methyl]imidazole;
1-[(2-(3'-bromo-4'-methoxy-4-biphenyl)-1,3-dioxolan-2-yl)methyl]imidazole;
1-[(2-(2-methoxy-4-biphenyl)-1,3-dioxan-2-yl)methyl]imidazole;
1-[(2-(4'-ethyl-4-biphenyl)-1,3-dioxan-2-yl)methyl]imidazole;
1-[(2-(4-methyl-5-chloro-3-biphenyl)-1,3-dioxolan-2-yl)methyl]imidazole;
1-[(2-(2'-methyl-4'-methoxy-4-biphenyl)-1,3-dioxolan-2-yl)methyl]imidazole;
1-[(2-(2'-ethyl-4'-methoxy-4-biphenyl)-1,3-dioxolan-2-yl)methyl]imidazole;
1-[(2-(2',4'-dimethoxy-4-biphenyl)-1,3-dioxolan-2-yl)methyl]imidazole;

1-[(2-(4'-methyl-2-biphenyl)-1,3-dioxolan-1-yl)methyl]imidazole;
1-[(2-(2'-t-butyl-2-biphenyl)-1,3-dioxolan-1-yl)methyl]imidazole;
1-[(2-(4'-bromo-2-biphenyl)-1,3-dioxolan-1-yl)methyl]imidazole;
1-[(2-(5-bromo-2-biphenyl)-1,3-dioxolan-1-yl)methyl]imidazole;
1-[(2-(2'-butyl-2-biphenyl)-1,3-dioxan-1-yl)methyl]imidazole;
1-[(2-(4'-bromo-2-biphenyl)-1,3-dioxan-1-yl)methyl]imidazole;
1-[(2-(5-bromo-2-biphenyl)-1,3-dioxan-1-yl)methyl]imidazole;
1-[(2-(3',5'-difluoro-2-biphenyl)-1,3-dioxan-1-yl)methyl]imidazole;
1-[(2-(3',4'-dimethyl-2-biphenyl)-1,3-dioxan-1-yl)methyl]imidazole;
1-[(2-(2'-propyl-4'-methoxy-4-biphenyl)-1,3-dioxolan-2-yl)methyl]imidazole;
1-[(2-(2',4'-dimethoxy-4-biphenyl)-1,3-dioxolan-2-yl)methyl]imidazole;
1-[(2-(2-methyl-4'-methoxy-4-biphenyl)-1,3-dioxolan-2-yl)methyl]imidazole;
1-[(2-(2'-ethyl-4'-methoxy-4-biphenyl)-4-methyl-1,3-dioxolan-2-yl)methyl]imidazole;
1-[(2-(2'-propyl-4'-methoxy-4-biphenyl)-4-methyl-1,3-dioxolan-2-yl)methyl]imidazole;
1-[(2-(2',4'-dimethoxy-4-biphenyl)-4-methyl-1,3-dioxolan-2-yl)methyl]imidazole;
1-[(2-(2-methyl-4'-methoxy-4-biphenyl)-4-methyl-1,3-dioxolan-2-yl)methyl]imidazole;
1-[(2-(2',4'-dimethoxy-4-biphenyl)-1,3-dioxan-2-yl)methyl]imidazole;
1-[(2-(2-methyl-4'-methoxy-4-biphenyl)-1,3-dioxan-2-yl)methyl]imidazole;
1-[(2-(2-methyl-2'-methyl-4'-methoxy-4-biphenyl)-1,3-dioxan-2-yl)methyl]imidazole;
1-[(2-(4-biphenyl)-4-n-propyl-1,3-dioxan-2-yl)methyl]imidazole;
1-[(2-(4-biphenyl)-4-n-butyl-1,3-dioxan-2-yl)methyl]imidazole;
1-[(2-(4-biphenyl)-5-methyl-1,3-dioxan-2-yl)methyl]imidazole;
1-[(2-(4-biphenyl)-5-ethyl-1,3-dioxan-2-yl)methyl]imidazole;

EXAMPLE II

This example illustrates the preparation of compounds according to formula I from formula II-type ketones.

A mixture of 1.84 g of 1-(2-(4-biphenyl)ethan-2-on-1-yl)imidazole, 2.66 g p-toluenesulfonic acid monohydrate, 5 ml ethylene glycol and 50 ml of toluene was refluxed through a Dean-Stark condenser for about 4 hours. After cooling, the reaction mixture was poured into 100 ml of dilute potassium carbonate, extracted with ether (3×75 ml) and the extracts dried over magnesium sulfate. The solvent was evaporated and the residue taken up in a small amount of ether and treated with ethereal hydrogen chloride until precipitation was complete. The resulting precipitate was filtered off and recrystallized from ethyl acetate/methanol to give 1-[(2-(4-biphenyl)-1,3-dioxolan-2-yl)methyl]imidazole hydrochloride, m.p. 262°–277°.

Similarly proceeding as above, but substituting the appropriate diol and the appropriate ketone in place of 1-(2-(4-biphenyl)ethan-2-on-1-yl)imidazole there may be prepared, for example, the following compounds:
1-[(2-(4-biphenyl)-1,3-dioxolan-2-yl)methyl]imidazole;
1-[(2-(4'-fluoro-4-biphenyl)-1,3-dioxolan-2-yl)methyl]imidazole;
1-[(2-(4'-trifluoromethyl-4-biphenyl)-1,3-dioxolan-2-yl)methyl]imidazole;
1-[(2-(4'-chloro-4-biphenyl)-1,3-dioxolan-2-yl)methyl]imidazole;
1-[(2-(4'-methyl-4-biphenyl)-1,3-dioxolan-2-yl)methyl]imidazole;
1-[(2-(4'-t-butyl-4-biphenyl)-1,3-dioxolan-2-yl)methyl]imidazole;
1-[(2-(4'-methoxy-4-biphenyl)-1,3-dioxolan-2-yl)methyl]imidazole;
1-[(2-(4-biphenyl)-4-methyl-1,3-dioxolan-2-yl)methyl]imidazole;
1-[(2-(4'-fluoro-4-biphenyl)-4-methyl-1,3-dioxolan-2-yl)methyl]imidazole;
1-[(2-(4'-trifluoromethyl-4-biphenyl)-4-methyl-1,3-dioxolan-2-yl)methyl]imidazole;
1-[(2-(4'-chloro-4-biphenyl)-4-methyl-1,3-dioxolan-2-yl)methyl]imidazole;
1-[(2-(4'-methyl-4-biphenyl)-4-methyl-1,3-dioxolan-2-yl)methyl]imidazole;
1-[(2-(4'-t-butyl-4-biphenyl)-4-methyl-1,3-dioxolan-2-yl)methyl]imidazole;
1-[(2-(4-biphenyl)-4-ethyl-1,3-dioxolan-2-yl)methyl]imidazole;
1-[(2-(4-biphenyl)-4-n-propyl-1,3-dioxolan-2-yl)methyl]imidazole;
1-[(2-(4-biphenyl)-4-n-butyl-1,3-dioxolan-2-yl)methyl]imidazole;
1-[(2-(4-biphenyl)-1,3-dioxan-2-yl)methyl]imidazole;
1-[(2-(4'-fluoro-4-biphenyl)-1,3-dioxan-2-yl)methyl]imidazole;
1-[(2-(4'-chloro-4-biphenyl)-1,3-dioxan-2-yl)methyl]imidazole;
1-[(2-(4'-methyl-4-biphenyl)-1,3-dioxan-2-yl)methyl]imidazole;
1-[(2-(4'-t-butyl-4-biphenyl)-1,3-dioxan-2-yl)methyl]imidazole;
1-[(2-(4'-trifluoromethyl-4-biphenyl)-1,3-dioxan-2-yl)methyl]imidazole;
1-[(2-(4-biphenyl)-4-methyl-1,3-dioxan-2-yl)methyl]imidazole;
1-[(2-(4'-fluoro-4-biphenyl)-4-methyl-1,3-dioxan-2-yl)methyl]imidazole;
1-[(2-(4'-chloro-4-biphenyl)-4-methyl-1,3-dioxan-2-yl)methyl]imidazole;
1-[(2-(4'-methoxy-4-biphenyl)-4-methyl-1,3-dioxan-2-yl)methyl]imidazole;
1-[(2-(4'-t-butyl-4-biphenyl)-4-methyl-1,3-dioxan-2-yl)methyl]imidazole;
1-[(2-(4'-trifluoromethyl-4-biphenyl)-4-methyl-1,3-dioxan-2-yl)methyl]imidazole;
1-[(2-(4'-fluoro-4-biphenyl)-5,5-dimethyl-1,3-dioxan-2-yl)methyl]imidazole;
1-[(2-(4'-chloro-4-biphenyl)-5,5-dimethyl-1,3-dioxan-2-yl)methyl]imidazole;
1-[(2-(4'-methyl-4-biphenyl)-5,5-dimethyl-1,3-dioxan-2-yl)methyl]imidazole;
1-[(2-(4'-t-butyl-4-biphenyl)-5,5-dimethyl-1,3-dioxan-2-yl)methyl]imidazole;
1-[(2-(4'-trifluoromethyl-4-biphenyl)-5,5-dimethyl-1,3-dioxan-2-yl)methyl]imidazole;
1-[(2-(4-biphenyl)-4-ethyl-1,3-dioxan-2-yl)methyl]imidazole;

1-[(2-(2-methoxy-4-biphenyl)-1,3-dioxolan-2-yl)methyl]imidazole;
1-[(2-(4'-ethyl-4-biphenyl)-1,3-dioxolan-2-yl)methyl]imidazole;
1-[(2-(4'-propyl-4-biphenyl)-1,3-dioxolan-2-yl)methyl]imidazole;
1-[(2-(4'-bromo-4-biphenyl)-1,3-dioxolan-2-yl)methyl]imidazole;
1-[(2-(3'-chloro-4'-methoxy-4-biphenyl)-1,3-dioxolan-2-yl)methyl]imidazole;
1-[(2-(3'-bromo-4'-methoxy-4-biphenyl)-1,3-dioxolan-2-yl)methyl]imidazole;
1-[(2-(2-methoxy-4-biphenyl)-1,3-dioxan-2-yl)methyl]imidazole;
1-[(2-(4'-ethyl-4-biphenyl)-1,3-dioxan-2-yl)methyl]imidazole;
1-[(2-(4'-propyl-4-biphenyl)-1,3-dioxan-2-yl)methyl]imidazole;
1-[(2-(4'-bromo-4-biphenyl)-1,3-dioxan-2-yl)methyl]imidazole;
1-[(2-(3'chloro-4'-methoxy-4-biphenyl)-1,3-dioxan-2-yl)methyl]imidazole;
1-[(2-(3'-bromo-4'-methoxy-4-biphenyl)-1,3-dioxan-2-yl)methyl]imidazole;
1-[(2-(4-methyl-5-chloro-3-biphenyl)-1,3-dioxolan-2-yl)methyl]imidazole;
1-[(2-(2'-methyl-4'-methoxy-4-biphenyl)-1,3-dioxolan-2-yl)methyl]imidazole;
1-[(2-(2'-ethyl-4'-methoxy-4-biphenyl)-1,3-dioxolan-2-yl)methyl]imidazole;
1-[(2-(2'-propyl-4'-methoxy-4-biphenyl)-1,3-dioxolan-2-yl)methyl]imidazole;
1-[(2-(2',4'-dimethoxy-4-biphenyl)-1,3-dioxolan-2-yl)methyl]imidazole;
1-[(2-(3'-methyl-2-biphenyl)-1,3-dioxolan-1-yl)methyl]imidazole;
1-[(2-(4'-methyl-2-biphenyl)-1,3-dioxolan-1-yl)methyl]imidazole;
1-[(2-(2'-t-butyl-2-biphenyl)-1,3-dioxolan-1-yl)methyl]imidazole;
1-[(2-(4'-bromo-2-biphenyl)-1,3-dioxolan-1-yl)methyl]imidazole;
1-[(2-(4'-chloro-2-biphenyl)-1,3-dioxolan-1-yl)methyl]imidazole;
1-[(2-(4-chloro-2-biphenyl)-1,3-dioxolan-1-yl)methyl]imidazole;
1-[(2-(4-bromo-2-biphenyl)-1,3-dioxolan-1-yl)methyl]imidazole;
1-[(2-(5-chloro-2-biphenyl)-1,3-dioxolan-1-yl)methyl]imidazole;
1-[(2-(5-bromo-2-biphenyl)-1,3-dioxolan-1-yl)methyl]imidazole;
1[(2-(3',5'-difluoro-2-biphenyl)-1,3 -dioxolan-1-yl)methyl]imidazole;
1-[(2-(3',4'-dimethyl-2-biphenyl)-1,3-dioxolan-1-yl)methyl]imidazole;
1-[(2-(3'-methyl-2-biphenyl)-1,3-dioxan-1-yl)methyl]imidazole;
1-[(2-(4'-methyl-2-biphenyl)-1,3-dioxan-1-yl)methyl]imidazole;
1-[(2-(2'-t-butyl-2-biphenyl)-1,3-dioxan-1-yl)methyl]imidazole;
1-[(2-(4'-bromo-2-biphenyl)-1,3-dioxan-1-yl)methyl]imidazole;
1-[(2-(4'-chloro-2-biphenyl)-1,3-dioxan-1-yl)methyl]imidazole;
1-[(2-(4-chloro-2-biphenyl)-1,3-dioxan-1-yl)methyl]imidazole;
1-[(2-(4-bromo-2-biphenyl)-1,3-dioxan-1-yl)methyl]imidazole;
1-[(2-(5-chloro-2-biphenyl)-1,3-dioxan-1-yl)methyl]imidazole;
1-[(2-(5-bromo-2-biphenyl)-1,3-dioxan-1-yl)methyl]imidazole;
1-[(2-(3',5'-difluoro-2-biphenyl)-1,3-dioxan-1-yl)methyl]imidazole;
1-[(2-(3',4'-dimethyl-2-biphenyl)-1,3-dioxan-1-yl)methyl]imidazole;
1-[(2-(4'-n-butoxy-4-biphenyl)-1,3-dioxolan-2-yl)methyl]imidazole;
1-[(2-(2-methyl-4'-methoxy-4-biphenyl)-1,3-dioxolan-2-yl)methyl]imidazole;
1-[(2-(2,2'-dimethyl-4'-methoxy-4-biphenyl)-1,3-dioxolan-2-yl)methyl]imidazole;
1-[(2-(3-methyl-4'-methoxy-4-biphenyl)-1,3-dioxolan-2-yl)methyl]imidazole;
1-[(2-(2,5-diethyl-4'-methoxy-4-biphenyl)-1,3-dioxolan-2-yl)methyl]imidazole;
1-[(2-(4'-methoxy-4-biphenyl)-4-methyl-1,3-dioxolan-2-yl)methyl]imidazole;
1-[(2-(2'-methyl-4'-methoxy-4-biphenyl)-4-methyl-1,3-dioxolan-2-yl)methyl]imidazole;
1-[(2-(2'-ethyl-4'-methoxy-4-biphenyl)-4-methyl-1,3-dioxolan-2-yl)methyl]imidazole;
1-[(2-(2'-propyl-4'-methoxy-4-biphenyl)-4-methyl-1,3-dioxolan-2-yl)methyl]imidazole;
1-[(2-(2',4'-dimethoxy-4-biphenyl)-4-methyl-1,3-dioxolan-2-yl)-methyl]imidazole;
1-[(2-(2-methyl-4'-methoxy-4-biphenyl)-4-methyl-1,3-dioxolan-2-yl)methyl]imidazole;
1-[(2-(4'-methoxy-4-biphenyl)-1,3-dioxan-2-yl)methyl]imidazole;
1-[(2-(2'-methyl-4'-methoxy-4-biphenyl)-1,3-dioxan-2-yl)methyl]-imidazole;
1-[(2-(2'-ethyl-4'-methoxy-4-biphenyl)-1,3-dioxan-2-yl)methyl]-imidazole;
1-[(2-(2'-propyl-4'-methoxy-4-biphenyl)-1,3-dioxan-2-yl)methyl]imidazole;
1-[(2-(2',4'-dimethoxy-4-biphenyl)-1,3-dioxan-2-yl)methyl]imidazole;
1-[(2-(2-methyl-4'-methoxy-4-biphenyl)-1,3-dioxan-2-yl)methyl]imidazole;
1-[(2-(2-methyl-2'-methyl-4'-methoxy-4-biphenyl)-1,3-dioxan-2-yl)methyl]imidazole;
1-[(2-(3-methyl-4'-methoxy-4-biphenyl)-1,3-dioxan-2-yl)methyl]imidazole;
1-[(2,5-diethyl-4'-methoxy-4-biphenyl)-1,3-dioxan-2-yl)methyl]imidazole;
1-[(2-(2'-propyl-4'-methoxy-4-biphenyl)-4-methyl-1,3-dioxan-2-yl)methyl]imidazole;
1-[(2-(2',4'-dimethoxy-4-biphenyl)-4-methyl-1,3-dioxan-2-yl)methyl]imidazole;
1-[(2-(2-methyl-4'-methoxy-4-biphenyl)-4-methyl-1,3-dioxan-2-yl)methyl]imidazole;
1-[(2-(2,2'-dimethyl-4'-methoxy-4-biphenyl)-4-methyl-1,3-dioxan-2-yl)methyl]imidazole;
1-[(2-(3-methyl-4'-methoxy-4-biphenyl)-4-methyl-1,3-dioxan-2-yl)methyl]imidazole;
1-[(2-(4-biphenyl)-4-n-propyl-1,3-dioxan-2-yl)methyl]imidazole;
1-[(2-(4-biphenyl)-4-n-butyl-1,3-dioxan-2-yl)methyl]imidazole;
1-[(2-(4-biphenyl)-5-methyl-1,3-dioxan-2-yl)methyl]imidazole;
1-[(2-(4-biphenyl)-5-ethyl-1,3-dioxan-2-yl)methyl]imidazole;

1-[(2-(4-biphenyl)-5-n-butyl-1,3-dioxan-2-yl)methyl]imidazole;
1-[(2-(4-biphenyl)-5,5-dimethyl-1,3-dioxan-2-yl)methyl]imidazole;
1-[(2-(3-biphenyl)-1,3-dioxan-2-yl)methyl]imidazole;
1-[(2-(2-biphenyl)-1,3-dioxan-2-yl)methyl]imidazole;

EXAMPLE III

Conversion of Free Bases to Salts

Ethereal hydrogen chloride is added dropwise to a stirred solution of 1-[(2-(4-biphenyl)-1,3-dioxolan-2-yl)methyl]imidazole in 30 ml of anhydrous ether until precipitation was complete. The product is filtered off, washed with ether, air-dried and recrystallized from methanol/ethyl acetate to yield 1-[(2-(4-biphenyl)-1,3-dioxolan-2-yl)methyl]imidazole hydrochloride, m.p. 262°–277° C.

In similar manner, all compounds of formula I in base form can be converted to their pharmaceutically acceptable acid addition salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, or salicylic acid, and the like.

EXAMPLE IV

Conversion of Salts to Free Bases

The compound 1-[(2-(4-biphenyl)-1,3-dioxan-2-yl)methyl]imidazole nitrate in 100 ml. of dichloromethane is shaken with excess dilute potassium carbonate solution until the salt was completely dissolved. The organic layer was then separated, washed twice with water, dried (MgSO₄) and evaporated to yield 1-[(2-(4-biphenyl)-1,3-dioxan-2-yl)methyl]imidazole as an oil.

In similar manner, the acid addition salts of all compounds of formula I as represented in Examples I and II can be converted to their corresponding compounds in base form.

EXAMPLE V

Direct Interchange of Acid Addition Salts

1-[(2-(4-biphenyl)-1,3-dioxan-2-yl)methyl]imidazole acetate in ethyl acetate is treated with ethereal hydrogen chloride until precipitation is just complete. The product is filtered off, dried, and recrystallized from methanol/acetone to yield 1-[(2-(4-biphenyl)-1,3-dioxan-2-yl)methyl]imidazole hydrochloride, m.p. 262°–277° C.

EXAMPLE VI

Anticonvulsant Activity-Maximal Electroshock Test

Initial anticonvulsant activity is determined by the "Anticonvulsant Activity-Maximal Electroshock Test" as described in J. Pharmacol. Exp. Ther. 106: 319–330, (1952) and the example below.

Groups of 10 male Hilltop ICR mice were utilized for these experiments. At a predetermined interval prior to testing, drug or vehicle was administered either i.p. or orally. At the appropriate time the mice were subjected to a transcorneal electroshock generated by a stimulator (Woolbury, L. A. and Davenport, V. D.: Design and use of a new electrochock seizure aparatus and analysis of factors altering seizure threshold and pattern. Arch. Intern. Pharmacokyn. Ther. 92: 97–107, 1952). The shock (50 mamp, 0.2 sec) elicited a three component seizure: tonic extension, tonic flexion and clonic seizures. The criterion of this test, the antagonism of the tonic extensor seizure was utilized as an endpoint. The quantal data accumulated from several doses of a test compound were utilized to determine an ED₅₀ (Litchfield, J. T. and Wilcoxon, F.: A Simplified Method of Evaluating Dose-effective Experiments. J. Pharmacol. Exp. Ther. 96: 99–113, 1949).

The oral ED₅₀ of 1-[(2-(4-biphenyl)-1,3-dioxolan-2-yl)-methyl]imidazole in mice at 30 minutes is 28 mg/kg. In rats the oral ED₅₀ of this compound at 30 minutes is 5.2 mg/kg.

EXAMPLE VII

The following pharmaceutical composition is representative of those which may be used for oral administration to a mammal for treating convulsions.

| Ingredients | Parts by Weight |
|---|---|
| Active ingredient | 200 |
| Magnesium stearate | 3 |
| Starch | 30 |
| Lactose | 116 |
| Polyvinylpyrrolidone | 3 |

The active ingredient, 1-[(2-(4-biphenyl)-1,3-dioxolan-2-yl)methyl]imidazole hydrochloride, is combined with the other ingredients and the mixture granulated using methanol as the solvent. The formulation is then dried and formed into tablets containing 200 milligrams of active compound with an appropriate tableting machine.

EXAMPLE VIII

Formulations suitable for intravenous and parenteral injection may be comprised of the following materials.

| Ingredient | % w/v |
|---|---|
| Active compound | 0.5 g |
| Propylene glycol | 20.0 g |
| Polyethylene glycol 400 | 20.0 g |
| Tween 80 | 1.0 g |
| 0.9% saline solution qs | 100 ml |

The active compound, 1-[(2-(4-biphenyl)-1,3-dioxolan-2-yl)methyl]imidazole hydrochloride, is dissolved in propylene glycol, polyethylene glycol 400 and Tween 80. A sufficient quantity of 0.9% saline solution is then added with stirring to provide 100 ml of the solution which is filtered through a 0.2 micron membrane filter and packaged under sterile conditions.

What is claimed is:

1. A method for treating convulsions in a mammal which method comprises administering to said mammal an effective amount of a compound of formula I

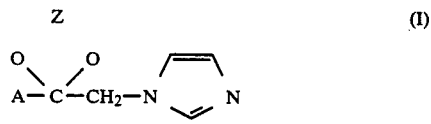

wherein

A is biphenyl unsubstituted or substituted on one or both rings with one or more halo, lower alkyl, lower alkoxy or trifluoromethyl substituent;

Z is ethylene unsubstituted or substituted with a single lower alkyl substituent or propylene unsubstituted or substituted with one or two lower alkyl substituents; or a pharmaceutically acceptable acid addition salt thereof either alone or in admixture with a pharmaceutically acceptable excipient.

2. The method of claim 1 wherein said compound is 1-[(2-(4-biphenyl)-1,3-dioxolan-2-yl)methyl]imidazole or a pharmaceutically acceptable acid addition salt thereof.